United States Patent [19]

Steinbrink, Jr.

[11] 4,078,892
[45] Mar. 14, 1978

[54] NOVEL MEANS AND METHOD FOR DIAGNOSTIC QUANTITATION OF SERUM OR PLASMA BILIRUBIN

[75] Inventor: Charles F. Steinbrink, Jr., Rockaway, N.J.

[73] Assignee: Becton, Dickinson and Company, Rutherford, N.J.

[21] Appl. No.: 724,307

[22] Filed: Sep. 17, 1976

Related U.S. Application Data

[63] Continuation of Ser. No. 591,775, June 30, 1975, abandoned.

[51] Int. Cl.² .................................................. G01N 33/16
[52] U.S. Cl. .................................. 23/230 B; 23/259; 206/219; 252/408
[58] Field of Search .............. 23/230 B, 259; 252/408

[56] References Cited

U.S. PATENT DOCUMENTS

| 3,068,855 | 12/1962 | Furlong | 23/230 B |
|---|---|---|---|
| 3,446,596 | 5/1969 | Salivar | 23/230 B |
| 3,449,081 | 6/1969 | Hughes | 23/253 R |
| 3,476,515 | 11/1969 | Johnson | 23/230 R |
| 3,511,607 | 5/1970 | Green | 23/230 B |
| 3,585,004 | 6/1971 | Mast | 23/253 TP |
| 3,652,222 | 3/1972 | Denney | 23/230 B |
| 3,814,586 | 6/1974 | Fraser | 23/230 B |
| 3,825,411 | 7/1974 | Morin | 23/230 B |
| 3,986,834 | 10/1976 | Steinbrink | 23/230 B |

Primary Examiner—Sidney Marantz
Attorney, Agent, or Firm—Kane, Dalsimer, Kane, Sullivan and Kurucz

[57] ABSTRACT

Method of determining total and direct bilirubin in blood serum or plasma. A first reagent containing sulfanilic and hydrochloric acids and a second reagent containing sulfanilic acid, hydrochloric acid and dimethyl sulfoxide are disposed in a scheme of reagent reservoirs. Into some of the reservoirs is also placed sodium nitrite contained in frangible capsules. The frangible capsules are broken with the resulting formation of a diazonium reagent. Blood serum or plasma, standard bilirubin solution and control serum are added to the reservoirs according to the analytical scheme. The subsequent color developments in the reservoirs are correlated to the bilirubin contents.

5 Claims, 5 Drawing Figures

NOVEL MEANS AND METHOD FOR DIAGNOSTIC QUANTITATION OF SERUM OR PLASMA BILIRUBIN

This is a continuation of application Ser. No. 591,775, filed June 30, 1975, now abandoned.

BACKGROUND OF THE INVENTION

1. Field of the Invention

The invention concerns diagnostic procedures performed on biological fluids and more particularly concerns a means and method of determining total and direct bilirubin concentrations in blood serum or plasma, employing diazonium salt reagents.

2. Brief Description of the Prior Art

Colorimetric techniques for the determination of bilirubin in blood were known prior to this invention; see for example Winsten et al., Clinical Chem., 14, (8), pps 850–1, (1968); Walters et al., Microchem. J., 13:253, (1968); Walters et al., Microchem. J., 15:231, (1970); U.S. Pat. Nos. 3,754,862 and 2,737,501. Although the prior art techniques include the use of diazonium salt reagents solubilized with dimethyl sulfoxide (see U.S. Pat. No. 3,511,607), such techniques have required performance by technical personnel having a fairly high degree of technical proficiency. One of the difficulties in total and direct bilirubin determinations employing as the reagent diazonium salts resides in the fact that such reagents are relatively unstable; see for example U.S. Pat. No. 2,737,501. Therefore, the reagent should be freshly prepared immediately before use in carrying out a blood analysis if accuracy is desired; see U.S. Pat. No. 3,652,222 which recommends that such reagents be used within 1 hour of preparation. Not only is a degree of technical proficiency required for the accurate preparation of a reliable reagent, but immediate-before-use preparation requires additional time and work on the part of the technician prior to his or her actually carrying out an analysis of an unknown specimen of blood serum or plasma.

The analysis kit of the present invention provides a means whereby a technician is provided with diazonium salt reagent precursors in such form that the reagent may be immediately prepared with a minimum of effort. The precursor reactants and consequently the kit per se is stable for a period of at least two years when stored out of direct sunlight and at room temperatures (below 86° F.). Furthermore, the analysis kit according to the method of this invention provides for the uniform preparation of control reagents. The kit which forms part of this invention also reduces the complexity of total and direct bilirubin analysis procedure so that it may be carried out by technicians having relatively little experience and training. The results of an analysis carried out employing the kit of the invention are uniform and compare remarkably well with more complex methods of determining bilirubin.

Bilirubin occurs in the blood in two forms, first in the free form or unconjugated and secondly as bilirubin glucuronide or conjugated bilirubin. Unconjugated bilirubin is formed as a decomposition product of erythrocytes and is conjugated and excreted into the bile by the liver. Conjugated bilirubin is measured as direct reading bilirubin and unconjugated bilirubin is quantitated by measuring total bilirubin and then subtracting direct reading bilirubin.

The method of the invention is particularly advantageous in that it permits for a highly accurate determination of total and direct bilirubin, with the expenditure of a minimum amount of time and effort on the part of technical personnel.

SUMMARY OF THE INVENTION

The invention comprises a kit for use in the rapid quantitative determination of total and direct bilirubin in blood and which has storage stability over a prolonged period of time, which comprises:

(a) a first set of four and a second set of three separate reagent reservoirs, each of which comprises a flexible walled, closed container having a thin puncturable zone for access to the contents of said reservoirs;

(b) an acid reagent consisting essentially of an aqueous solution of sulfanilic and hydrochloric acids disposed in each of said reservoirs in said first set;

(c) an acid reagent consisting essentially of an aqueous solution of sulfanilic and hydrochloric acids and dimethyl sulfoxide disposed in each of said reservoirs in said second set;

(d) means disposed within each of said reservoirs of said second set and in one of said reservoirs of said first set, for enclosing under hermetic conditions a proportion of sodium nitrite;

(e) sodium nitrite enclosed by said means;

(f) means for bringing said sodium nitrite into admixture with the acid reagent contained in the same reservoir within which said sodium nitrite is disposed; and (g) means for packaging said kit in a unitary package so that all parts of said kit are conveniently available when needed.

The kit of the invention has a shelf-like stability of at least 2 years.

The invention also comprises an improved method for the determination of total bilirubin in blood serum or plasma, which comprises;

(a) providing a kit, which comprises:

(1) a first set of three separate reagent reservoirs, each of which comprises a flexible walled, closed container having a thin puncturable zone for access to the contents of said reservoirs, one of said reservoirs being identified as a "control reservoir," one of said reservoirs being identified as a "standard reservoir" and one of said reservoirs being identified as an "unknown reservoir";

(2) a second set of three separate reagent reservoirs, each of which comprises a flexible walled, closed container having a thin puncturable zone for access thereto, one of said third set of reservoirs being identified as a "control blank reservoir," one of said third set of reservoirs being identified as a "standard blank reservoir" and one of said third set of reservoirs being identified as an "unknown blank reservoir";

(3) a first acid reagent consisting essentially of an aqueous solution of sulfanilic and hydrochloric acids and dimethyl sulfoxide disposed in each of said first set of reservoirs;

(4) a second acid reagent consisting essentially of an aqueous solution of sulfanilic and hydrochloric acids disposed in each of said second set of reservoirs;

(5) means disposed within each of said first set of reservoirs for enclosing under hermetic conditions a proportion of sodium nitrite;
(6) sodium nitrite enclosed by said means;
(7) means for bringing said sodium nitrite into admixture with the acid reagent contained in the same reservoir within which said sodium nitrite is disposed;

(b) activating each of said means for bringing said sodium nitrite into admixture with said acid reagent;

(c) adding equally measured proportions of blood serum or plasma to each of the reservoirs identified as "unknown reservoir," and "unknown blank reservoir";

(d) adding equally measured proportions of a standard bilirubin solution to each of the two reservoirs identified as "standard reservoir" and "standard blank reservoir";

(e) adding equally measured proportions of a control serum to each of the two reservoirs identified as "control reservoir" and "control blank reservoir";

(f) incubating the mixtures obtained in steps (c) – (e) above at room temperature for about 10 minutes.

(g) observing the degree of color developed in each of said reservoirs within about 30 minutes of said incubating; and (h) comparing the degree of color developed in each of said reservoirs.

The invention also comprises a method of determining the direct bilirubin content of blood serum or plasma.

The method of determining direct bilirubin in blood serum or plasma comprises;

(a) providing
a first set of one and a second set of three separate reagent reservoirs, each of which comprises a flexible walled, closed container having a thin puncturable zone for access to the contents of said reservoirs and which contain;
  (i) a first acid reagent consisting essentially of an aqueous solution of sulfanilic and hydrochloric acids disposed in said reservoir in said first set;
  (ii) a second acid reagent consisting essentially of an aqueous solution of sulfanilic and hydrochloric acids and dimethyl sulfoxide disposed in each of said reservoirs in said second set;
  (iii) a frangible capsule disposed within each of said reservoirs and enclosing under hermetic conditions a proportion of sodium nitrite;

(b) breaking each of said capsules within said reservoirs, thereby bringing said sodium nitrite into admixture with the acid reagent in said reservoirs;

(c) adding equally measured proportions of blood serum or plasma to one reservoir of each of said sets;

(d) adding a measured proportion of a standard bilirubin solution to a second reservoir in said second set;

(e) adding a measured proportion of a control serum to the remaining reservoir of said second set;

(f) simultaneously incubating the mixtures obtained in steps (c) – (e) above at room temperature for about 10 minutes;

(g) observing the degree of color developed in each of said reservoirs within about thirty minutes of said incubating; and (h) comparing the degree of color developed in each of said reservoirs to determine direct bilirubin in the mixtures of step (c) above.

DETAILED DESCRIPTION OF THE INVENTION

Figure 1:
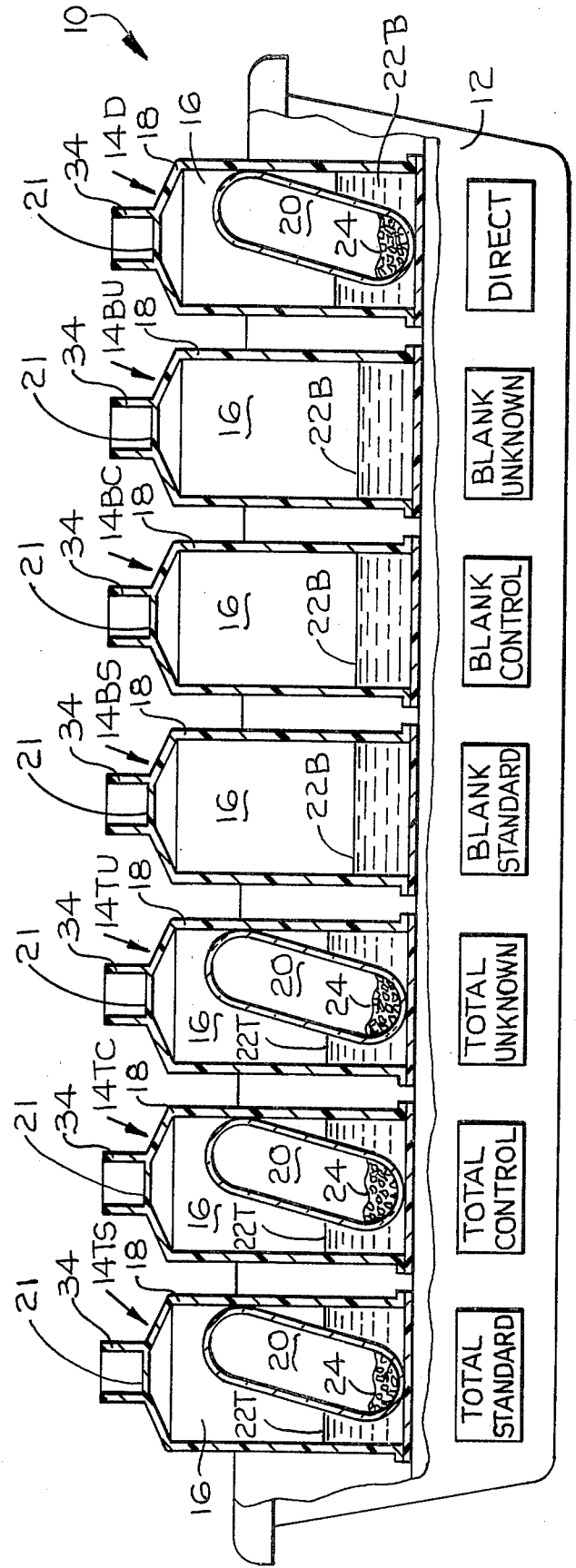
FIG. 1 is a cross-sectional, in part, side elevation of an embodiment kit for the rapid determination of total and direct bilirubin in blood serum or plasma.

A complete understanding of the invention may be conveniently had by referring to the accompanying drawings of FIGS. 1-5, inclusive. Referring first to FIG. 1, there is seen a kit 10 which comprises a tray 12 shown cut away, in part, to show in cross-sectional side elevation, seven identical vessels 14TS, 14TC, 14TU, 14BS, 14BC, 14BU and 14D. Vessel 14TS is positioned to correspond to a marker "total standard" vessel, vessel 14TC is positioned to correspond to a marker "total control," vessel 14TU is positioned in tray 12 to correspond to a marker "total unknown," vessel 14BS is positioned adjacent to a marker "blank standard," vessel 14BC is positioned adjacent to a marker "blank control," vessel 14BU is positioned adjacent marker "blank unknown" and vessel 14D is positioned adjacent to a marker "direct." Any alternative system of identification may be employed to indicate the function of the vessels as will be described more fully hereinafter. For example, the markers may be placed on the appropriate vessels themselves, the vessels may be color coded, or the vessels may be numbered according to an identifiable code. Each vessel 14 is a reagent reservoir which comprises a completely enclosed chamber defined by flexible walls 18, which may be constructed of any flexible polymeric material such as for example, polyethylene, polypropylene and like polymeric materials which are relatively inert chemically and highly flexible. Contained by the flexible walls 18 of each vessel 14TS, 14TC and 14TU is a frangible capsule 20 and 2.0 milliliters of acid reagent solution 22T. Acid reagent solution 22T is prepared by admixture of 18.3 mg. of sulfanilic acid, 128.8 ml. of hydrochloric acid, 4.22 gms. of dimethyl sulfoxide and sufficient distilled water to make 1 liter of acid reagent solution 22T. Frangible capsule 20 may be a thin walled glass capsule which in vessels 14TS, 14TC and 14TU hermetically seals and encloses 8.7 mg. of sodium nitrite 24.

Each of vessels 14BS, 14BC and 14BU contain 2.0 ml of acid reagent solution 22B, prepared by admixture of 26.2 mg. of sulfanilic acid, 184.2 ml. of hydrochloric acid and sufficient water to make 1 liter.

Vessel 14D also holds 2.0 ml. of acid reagent 22B and also a frangible capsule 20 which hermetically encapsulates 2.9 mg. of sodium nitrite 24.

Entry into the vessels 14 may be obtained by puncturing relatively thin zone 21 in the wall 18 of the vessels. Adjacent to the thin zone 21 is a hub 34 integrally formed with wall 18. Hub 34 is to receive a micropipette as will be discussed hereinafter.

Those skilled in the art will appreciate that the preferred embodiments described above and which comprise a kit 10 within the scope of the invention may be modified in a number of ways without departing from the spirit of the invention. For example, other sizes, shapes and forms of vessels 14 may be employed. Similarly, other packaging means such as racks, holders, preformed dishes, and the like may be substituted for tray 12 to provide a unitary package. In addition, additional components may be employed to prepare a kit within the scope of the invention. For example, a puncturing tool may be provided for puncturing thin zone 21 when entry into chamber 16 of any one of the vessels 14 is required. A pipette or syringe 28 may also be included in the kit for the transfer of reagent, specimens undergoing analysis and like materials as will be discussed hereinafter. The unitary package provides a convenient means for providing all of the necessary articles of use in carrying out the method of the invention.

Figure 2:
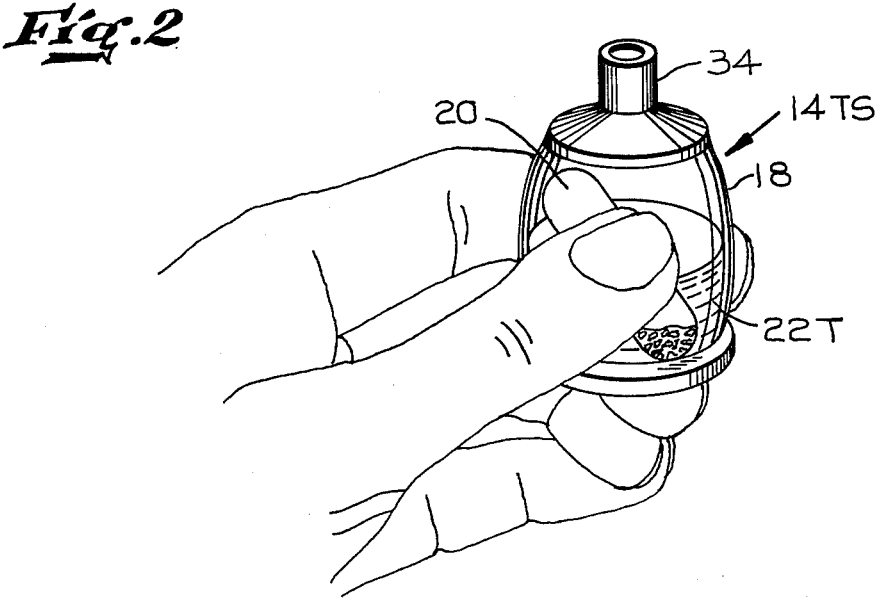
FIG. 2 is an isometric view of a vessel component of the embodiment kit shown in FIG. 1, during activation to prepare a fresh diazo reagent for determination of total and direct bilirubin.
Figure 3:
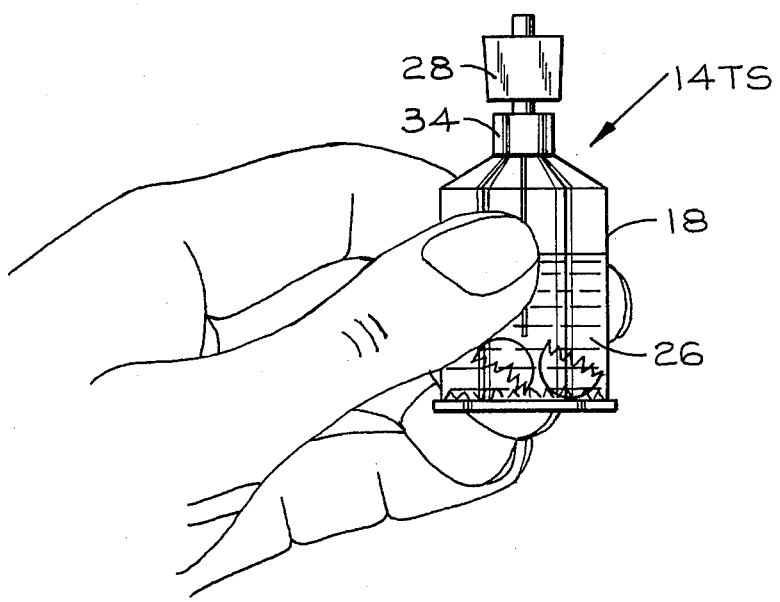
FIG. 3 is an isometric view as in FIG. 2 but after introduction of blood serum or plasma to the freshly prepared diazo reagent.

To carry out the method of the invention, each of the vessels 14TS, 14TC, 14TU and 14D are taken from tray 12, in turn, and the flexible walls 18 squeezed manually as shown in FIG. 2, to break (showing vessel 14TS) the frangible capsule 20 enclosed in chamber 16. Upon breaking of frangible capsule 20, the sodium nitrite 24 is admixed with acid reagent solution 22T or 22B to provide a freshly prepared solution of nitrous acid (I). The nitrous acid (I) reacts with the p-sulfanilic acid (II) to obtain p-benzene diazonium sulfonate (III) which is reagent mixture 26 as shown in FIG. 3.

The reaction is shown schematically by the equations:

1. $NaONO + H^+ \longrightarrow HONO + Na^+$
 (I)

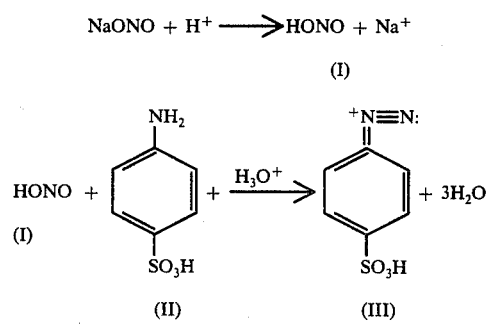

Figure 4:
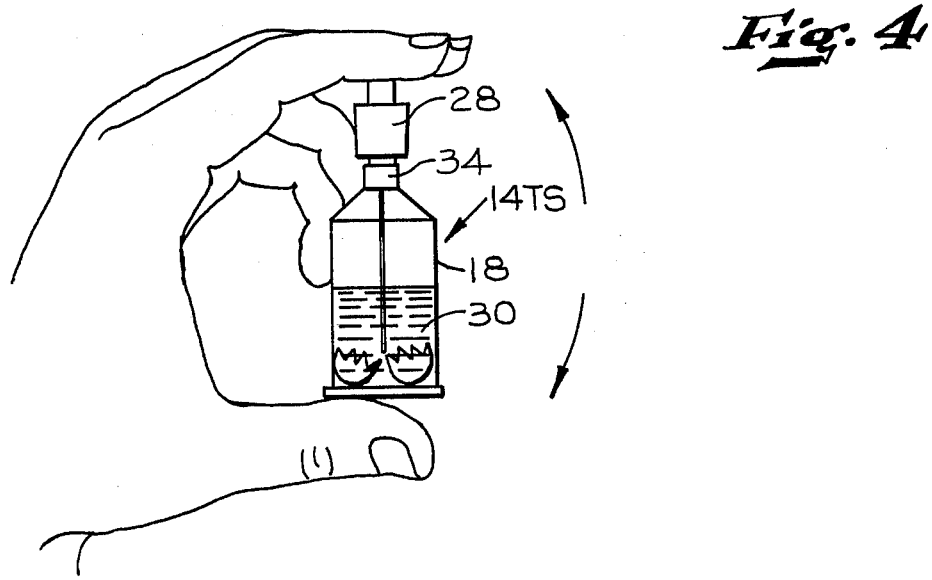
FIG. 4 is an isometric view as seen in FIG. 3, showing mixing of the freshly prepared diazo reagent and a blood serum or plasma specimen.

Within one hour following the fresh preparation of reagent 26 by admixture of reagent 22T and 22B with 24, a puncture is made in thin zone 21 of each of the vessels 14. Through the puncture in each of vessels 14TU, 14BU and 14D there is introduced into chamber 16, 50 ml. of the serum or plasma to be analyzed for its bilirubin content. To each of vessels 14TS and 14BS there is introduced into their respective chambers 16, 50 ml. of a standard solution of bilirubin. Standard bilirubin concentrates are commercially available and their preparation is well known; see for example Walters et al., (1968), supra. and U.S. Pat. No. 2,770,601. To each of vessels 14TC and 14BC there is introduced 50 ml. of a protein based bilirubin control, free of bilirubin. Such control solutions are well known; see for example Walters et al., (1968), supra. at page 254. A convenient means of introducing the serum, plasma or standard solution into the vessels 14 is with a measuring micropipette 28 adapted to mate with and be received by hub 34 as shown in FIG. 3. After the unknown blood serum or plasma control and standards are introduced into the vessels 14, the vessels are shaken to assure a complete admixture of the mixtures contained therein. As shown in FIG. 4, a convenient method of carrying out the admixture is by shaking each of the vessels 14 manually with micropipette 28 in place, whereupon there is obtained a different reaction mixture 30 in each vessel 14. The micropipette 28 is retained in place as a convenience to close the puncture made in each vessel during admixture.

Upon introduction of bilirubin (IV) to any one of the acid reagents 26, a colored compound (azobilirubin) (V) is formed according to the reaction scheme:

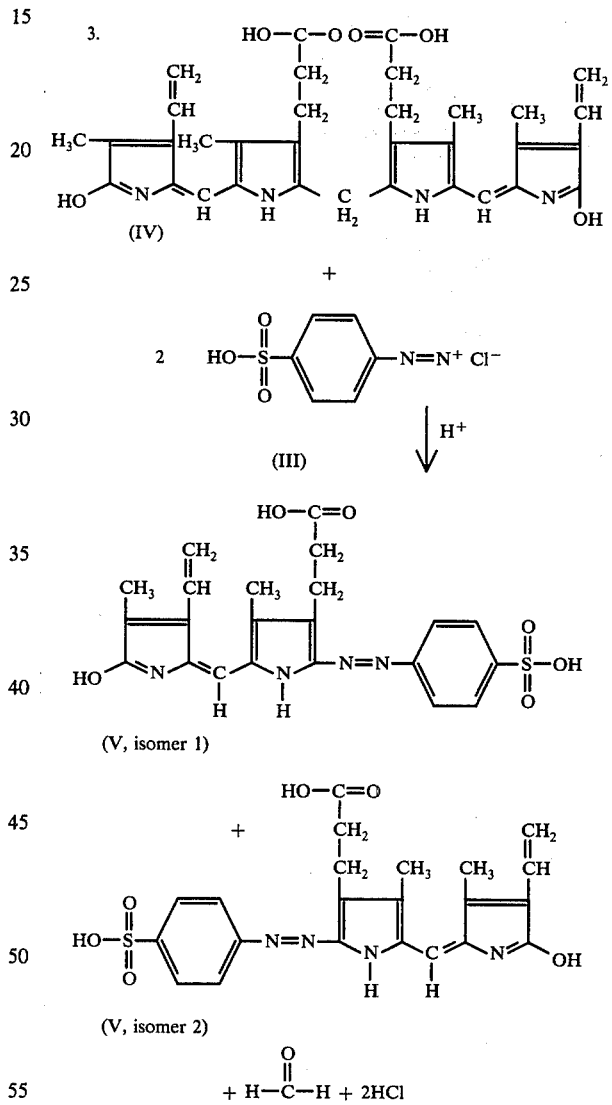

As shown in the reaction scheme, the colored azobilirubin (V) has two isomeric forms. The azobilirubin (V) has a purple-violet color and the degree of color is directly proportionate to the azobilirubin concentration. Thus one can readily calculate the concentration of azobilirubin by comparison to the known reference standard and the starting concentration of bilirubin is accordingly calculated.

Figure 5:
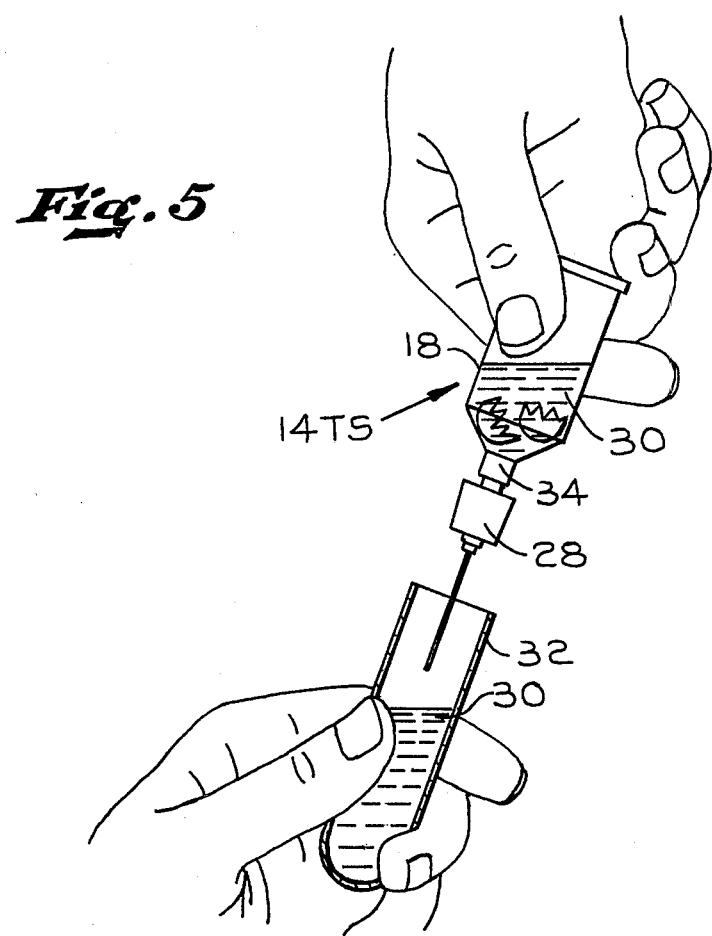
FIG. 5 shows transfer of the mixed blood serum or plasma with diazo reagent, to a test tube for further processing according to the method of the invention.

Following the introduction of unknown, standard and controls into the vessels 14, the resulting mixtures 30 are allowed to incubate at room temperature for about 10 minutes to allow completion of the reaction and full color development. Within about 30 minutes of incubation, the mixtures 30 in each vessel 14 are transferred from each of vessels 14 to a correspondingly identified or labeled cuvette 32. As shown in FIG. 5, with vessel 14TS, transfer may be conveniently carried out by reversing micropipette 28 in hub 34 and squeezing walls 18 to force the transfer. The cuvettes 32 are inserted in the reading station of a spectrophotometer for the measurement of the light absorbance of the contained mixtures. Setting the wavelength on the spectrophotometer at 560 nm, maximum optical density measurements on each of the seven mixtures 30 are obtained. The measurement should be taken within at least 30 minutes after the incubating step described above.

After determining the maximum optical density of the unknown reaction mixtures 30 (from vessels 14TU, 14BU and 14D) and the standard reaction mixtures 30 from 14TS and 14BS vessels, the concentration of total bilirubin in the unknown may be calculated according to the formula:

$$\frac{\text{Optical density Unknown (Vessel 14TU)}}{\text{Optical density Standard (Vessel 14TS)}} \times \begin{array}{c}\text{Concentration}\\\text{of Standard}\\\text{Added in vessel}\\\text{14TS (Mg/dl)}\end{array} = \begin{array}{c}\text{Total}\\\text{Bilirubin}\\\text{(Mg/dl)}\end{array}$$

The concentration of direct bilirubin in the unknown may be calculated according to the formula:

$$\frac{\text{Optical density Unknown (Vessel 14D)}}{\text{Optical density Standard (Vessel 14TS)}} \times \begin{array}{c}\text{Concentration}\\\text{of Standard}\\\text{Added in vessel}\\\text{14TS (Mg/dl)}\end{array} = \begin{array}{c}\text{Direct}\\\text{Bilirubin}\\\text{(mg/dl)}\end{array}$$

The mixtures 30 carried through the above procedure from reservoir vessels 14BU, 14BS, 14CU and 14CS are the controls and should present a clear to pale amber color. If there is a notable discoloration in any of the latter, such is an indication that the analysis procedure was contaminated, and a re-analysis is warranted.

What is claimed:

1. A method for the determination of total bilirubin in blood serum or plasma, which comprises:
   (a) providing a first set of three and a second set of three separate reagent reservoirs, each of which comprises a flexible walled, closed container having a thin puncturable zone for access to the contents of said reservoirs and which contain:
      (i) a first acid reagent consisting essentially of an aqueous solution of sulfanilic and hydrochloric acids disposed in each of said reservoirs in said first set;
      (ii) a second acid reagent consisting essentially of an aqueous solution of sulfanilic and hydrochloric acids and dimethyl sulfoxide disposed in each of said reservoirs in said second set;
      (iii) a frangible capsule disposed within each of said reservoirs of said second set and enclosing under hermetic conditions a proportion of sodium nitrite;
   (b) breaking each of said capsules within said reservoirs thereby bringing said sodium nitrite into admixture with the acid reagent;
   (c) adding equally measured proportions of blood serum or plasma to one reservoir of each of said sets;
   (d) adding equally measured proportions of a standard bilirubin solution to a second reservoir of each of said sets;
   (e) adding equally measured proportions of a control serum to each of a third reservoir in each of said sets;
   (f) simultaneously incubating the mixtures obtained in steps (c) – (e) above at room temperature for about ten minutes;
   (g) observing the degree of color developed in each of said reservoirs within about 30 minutes of said incubating; and
   (h) comparing the degree of color developed in each of said reservoirs to determine total bilirubin in the mixture of step (c) above.

2. A method according to claim 1 wherein said observing is with the aid of a spectrophotometer.

3. A method for the determination of direct bilirubin in blood serum or plasma, which comprises;
   (a) providing a first set of one and a second set of three separate reagent reservoirs, each of which comprises a flexible walled, closed container having a thin puncturable zone for access to the contents of said reservoirs and which contain;
      (i) a first acid reagent consisting essentially of an aqueous solution of sulfanilic and hydrochloric acids disposed in said reservoir in said first set;
      (ii) a second acid reagent consisting essentially of an aqueous solution of sulfanilic and hydrochloric acids and dimethyl sulfoxide disposed in each of said reservoirs in said second set;
      (iii) a frangible capsule disposed within each of said reservoirs of said second set and enclosing under hermetic conditions a proportion of sodium nitrite;
   (b) breaking each of said capsules within said reservoirs, thereby bringing said sodium nitrite into admixture with the acid reagent in said reservoirs;
   (c) adding equally measured proportions of blood serum or plasma to one reservoir of each of said sets;
   (d) adding a measured proportion of a standard bilirubin solution to a second reservoir in said second set;
   (e) adding a measured proportion of a control serum to the remaining reservoir of said second set;
   (f) simultaneously incubating the mixtures obtained in steps (c) – (e) above at room temperature for about 10 minutes;
   (g) observing the degree of color developed in each of said reservoirs within about 30 minutes of said incubating; and
   (h) comparing the degree of color developed in each of said reservoirs to determine direct bilirubin in the mixtures of step (c) above.

4. A method according to claim 3 wherein said observing is with the aid of a spectrophotometer.

5. A method for the determination of total and direct bilirubin in blood serum or plasma, which comprises;
   (a) providing a first set of four and a second set of three separate reagent reservoirs, each of which comprises a flexible walled, closed container having a thin puncturable zone for access to the contents of said reservoirs and which contain:
      (i) a first acid reagent consisting essentially of an aqueous solution of sulfanilic and hydrochloric acids disposed in each of said reservoirs in said first set;

(ii) a second acid reagent consisting essentially of an aqueous solution of sulfanilic and hydrochloric acids and dimethyl sulfoxide disposed in each of said reservoirs in said second set;

(iii) a frangible capsule disposed within each of said reservoirs of said second set and one of said reservoirs of said first set, each capsule enclosing under hermetic conditions a proportion of sodium nitrite;

(b) breaking each of said capsule within said reservoirs thereby bringing said sodium nitrite into admixture with the acid reagent;

(c) adding equally measured proportions of blood serum or plasma to two reservoirs of said first set and one reservoir of said second set;

(d) adding equally measured proportions of a standard bilirubin solution to a third reservoir in said first set and to a second reservoir in said second set;

(e) adding equally measured proportions of a control serum to each of the remaining reservoirs in said first and second sets;

(f) simultaneously incubating the mixtures obtained in steps (c) – (e) above at room temperature for about 10 minutes;

(g) observing the degree of color developed in each of said reservoirs within about thirty minutes of said incubating; and (h) comparing the degree of color developed in each of said reservoirs to determine total and direct bilirubin in the mixtures of step (c) above.

* * * * *